(12) United States Patent
Shonk

(10) Patent No.: US 7,329,016 B1
(45) Date of Patent: Feb. 12, 2008

(54) FOOT INSPECTION MIRROR

(76) Inventor: Helen Shonk, 1267 Cedarwood Way, Uniontown, OH (US) 44685

( * ) Notice: Subject to any disclaimer, the term of this patent is extended or adjusted under 35 U.S.C. 154(b) by 0 days.

(21) Appl. No.: 11/595,633

(22) Filed: Nov. 9, 2006

Related U.S. Application Data

(60) Provisional application No. 60/597,128, filed on Nov. 11, 2005.

(51) Int. Cl.
G02B 5/08 (2006.01)
G02B 7/182 (2006.01)
F21V 33/00 (2006.01)

(52) U.S. Cl. .............. 359/854; 359/850; 359/872; 362/140; 362/135; 248/471; 248/474; 248/469

(58) Field of Classification Search ......... 359/850, 359/854, 855, 884, 872; 362/135, 140, 142; 248/469, 474, 471, 472
See application file for complete search history.

(56) References Cited

U.S. PATENT DOCUMENTS

| 518,382 | A | * | 4/1894 | Wiederer | 359/854 |
| 907,420 | A | * | 12/1908 | Sollis | 359/855 |
| 1,643,626 | A | | 9/1927 | May | |
| 2,136,832 | A | | 11/1938 | Weisberger | |
| 2,480,361 | A | * | 8/1949 | Doumitt | 600/592 |
| 4,120,563 | A | | 10/1978 | Stefanou | |
| 4,257,680 | A | | 3/1981 | Baczkowski | |
| 4,520,581 | A | | 6/1985 | Irwin et al. | |
| 4,645,714 | A | * | 2/1987 | Roche et al. | 428/458 |
| 4,745,290 | A | | 5/1988 | Frankel et al. | |
| 5,392,162 | A | * | 2/1995 | Glucksman | 359/872 |
| 5,568,965 | A | | 10/1996 | Eagan | |
| 5,915,825 | A | | 6/1999 | Weister | |
| 6,305,809 | B1 | * | 10/2001 | Zadro | 359/840 |
| 6,382,807 | B1 | * | 5/2002 | Chandross et al. | 359/883 |
| 6,598,992 | B1 | | 7/2003 | Ames | |
| 6,834,655 | B1 | | 12/2004 | Briscoe | |
| 7,090,378 | B1 | * | 8/2006 | Zadro | 362/298 |
| 2005/0146863 | A1 | * | 7/2005 | Mullani | 362/140 |
| 2007/0091487 | A1 | * | 4/2007 | DeFazio et al. | 359/859 |

* cited by examiner

Primary Examiner—Ricky D. Shafer
(74) Attorney, Agent, or Firm—John D. Gugliotta; Mandy Seuffert

(57) ABSTRACT

The present invention relates generally to a foot inspection mirror and, more particularly, to a foot inspection device comprised of an assembly of mirrors positioned in such an array so as to assist diabetics and other users in visually self-inspecting all sides of an illuminated foot without unnecessary standing or maneuvering. The instant abstract is neither intended to define the invention disclosed in this specification nor intended to limit the scope of the invention in any way.

17 Claims, 4 Drawing Sheets

FOOT INSPECTION MIRROR

RELATED APPLICATIONS

The present invention claims the benefit of U.S. Provisional Patent No. 60/597,128, filed Nov. 11, 2005. The entire disclosure and contents of the above application is hereby incorporated by reference.

BACKGROUND OF THE INVENTION

1. Field of the Invention

The present invention relates generally to a foot inspection mirror and, more particularly, to a foot inspection device comprised of an assembly of mirrors positioned in such an array so as to assist diabetics and other users in visually self-inspecting all sides of an illuminated foot without unnecessary standing or maneuvering.

2. Description of the Related Art

Diabetics are especially susceptible to both cardiovascular disease, which reduces blood flow to the feet, and nerve damage, which causes numbness in the feet. Oftentimes, diabetics aren't aware that an ulcer or sore is developing on the bottom of their feet because they experience a loss of feeling. A common problem with abnormalities that go unnoticed is that they lead to amputation. One key component to preventative diabetic foot care is to visually examine foots regularly. Early detection of irritations can prevent the development of severe ulcers or infections. The problem with routine visual examinations, however, is that many elderly and overweight diabetics experience difficulty reaching their feet.

As is well known in the art, there are a number of foot inspection devices provided to diabetics for self-monitoring foot health. These devices are most commonly comprised of mirrors and illuminating lamps, but their construction tends to be small or difficult to use. A search of the prior art did not disclose any patents that read directly on the claims of the instant invention; however, the following references were considered related.

Of considerable relevance is U.S. Pat. No. 6,598,992, issued on Jul. 29, 2003, which discloses a portable foot inspection mirror having a magnified reflective surface, a frame surrounding the perimeter of the reflective surface, and a small high intensity light directed downward toward the reflective surface. One of the device's disadvantages is its construction. The light is positioned at the distal end of a curved rod connected to the frame. The light is positioned to adequately illuminate the back or side of the foot, but its position fails to fully illuminate the underside of the foot. In fact, light is emitted from behind the foot, so the foot itself can actually obstruct the light path if it is positioned in the center of the mirror. The device also comprises only one flat mirror, so a person is required to maneuver his or her foot to inspect it one side at a time.

The foot inspection and recording device disclosed in U.S. Pat. No. 2,136,832, issued Nov. 15, 1938, teaches two side walls extending upwards from a glass supporting member to form a box-like cabinet, a mirror located angularly below the glass, and similarly positioned mirrors located at the opposite sides of the cabinet above the glass. Lamps located behind the glass bottom, adjacent to the opposite side walls, illuminate the mirror. There are two problems with this device. First, the very purpose of observing the underside of a foot is hindered when a person is required to stand on the device. Secondly, the mirrors and lamps are positioned to better record and print the condition of the foot verses inspect it. The device is too bulky and complex for simple use.

The foot-care accessory kit disclosed in U.S. Pat. No. 6,834,655, issued on Dec. 28, 2004, comprises a plurality of light bulbs disposed about the perimeter of a mirror in the shape of a foot. The device further comprises an elongated handle for pivotally moving the mirror when a person is inspecting the lower appendages of the foot. The mirror is too small to view the entire foot at one time and it requires unnecessary maneuvering of both the mirror and foot to conduct an examination. This can be especially cumbersome to the elderly, overweight or people who experience difficulty with flexibility and movement.

While the foregoing features disclosed in the prior art are incorporated into this invention, other elements are different enough as to make the combination distinguished over the inventor's own prior art. Consequently, a need has been long-felt for a foot inspection device comprised of an assembly of mirrors constructed in such a way as to assist the user in visually self-inspecting all sides of an illuminated foot without unnecessary standing or maneuvering.

SUMMARY OF THE INVENTION

It is therefore an object of the present invention to provide an improved foot inspection device that allows a user to quickly and efficiently conduct a visual examination of his or her foot. In accordance with the preferred embodiment, the foot inspection mirror comprises a mirror assembly portion that is pivotally supported by a stand portion. The stand portion comprises a base provided to support the foot inspection mirror on floors and flat surfaces.

The mirror assembly portion preferably comprises a plurality of five individual mirrors arranged in a fixed array that allows a user to quickly and efficiently conduct a visual inspection of all portions of his or her feet, one at a time. It is a feature of the present invention to provide a magnifying mirror, preferably being the largest of the plurality of mirrors. It is another feature of the present invention to position two smaller mirrors adjacent to the vertical sides of the largest mirror. These mirrors are angled toward each other and facilitate inspection of the underside and sides of a foot. Two additional mirrors extend outwards from the bottom sides of the first three mirrors and meet at opposing sides. These mirrors are angled downwards towards one another and facilitate inspection of the heel of a foot. It is a further advantage to the present invention if the mirror assembly comprises all magnifying mirrors.

The foot inspection mirror according to the present invention further comprises a plurality of lighting elements, i.e. light emitting diodes (LED) to illuminate the user's foot during inspection. The lights surround the perimeter of the mirrors and are angled to illuminate the entire foot regardless of the ambient room lighting. The lights are powered by batteries, thus eliminating the tripping hazard of an electrical cord. A large switch positioned at the top of the device handle is easily accessible for turning the lights on and off. An automatic off-timer saves battery.

The foot inspection mirror according to the invention can be produced in a variety of aesthetically pleasing colors and materials and is thus particularly suitable for placement on the floor next to a user's bed, in a user's bathroom or at any other location that encourages daily foot inspection. The user, in the course of a normal day, can view both of his or her feet, one at a time, in a matter of seconds. Presently available commercial products for self-inspection of feet are unsightly and must be stored elsewhere (e.g., in drawers or cabinets), which contributes to patients forgetting to inspect their feet. Some presently available commercial products require users to hold the inspection device while inspecting their feet. Other products do not allow the user to sit and have a clear and complete view of the foot. The foot inspection mirror according to the present invention, with its pivoting mirror assembly portion, allows the user to sit or stand for a complete, clear view of the foot. The feature is important to obese and elderly patients or other persons who experience difficulty with flexibility and balance. The LED lights are positioned to illuminate the foot and angled to highlight calluses and raised areas. The foot inspection mirror aids in the early detection of calluses, sores and infections that lead to amputation.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures;

1. Detailed Description of the Figures

Figure 1:
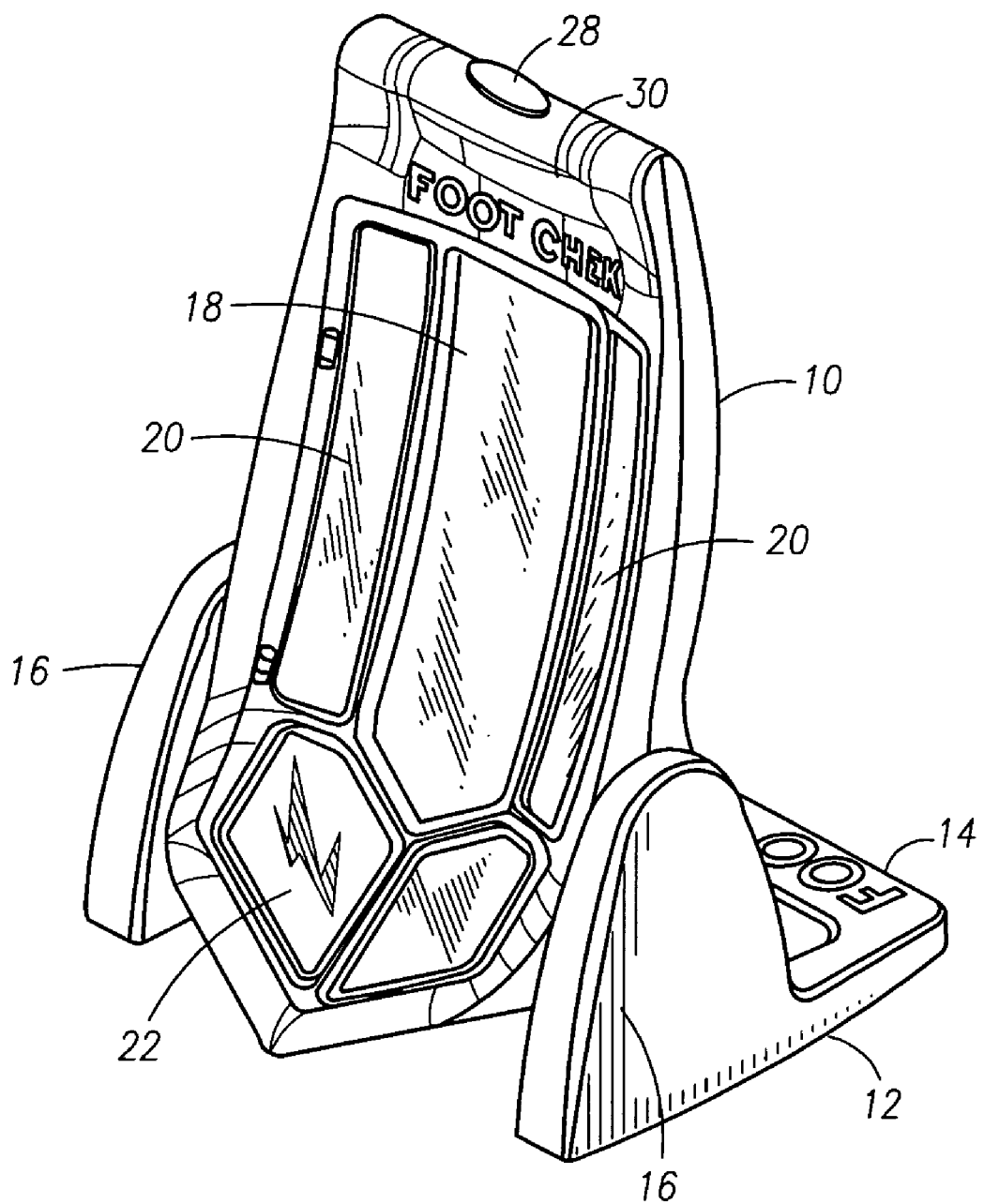
FIG. 1 is a perspective view of a preferred embodiment of a foot inspection mirror according to the invention.
Figure 2:
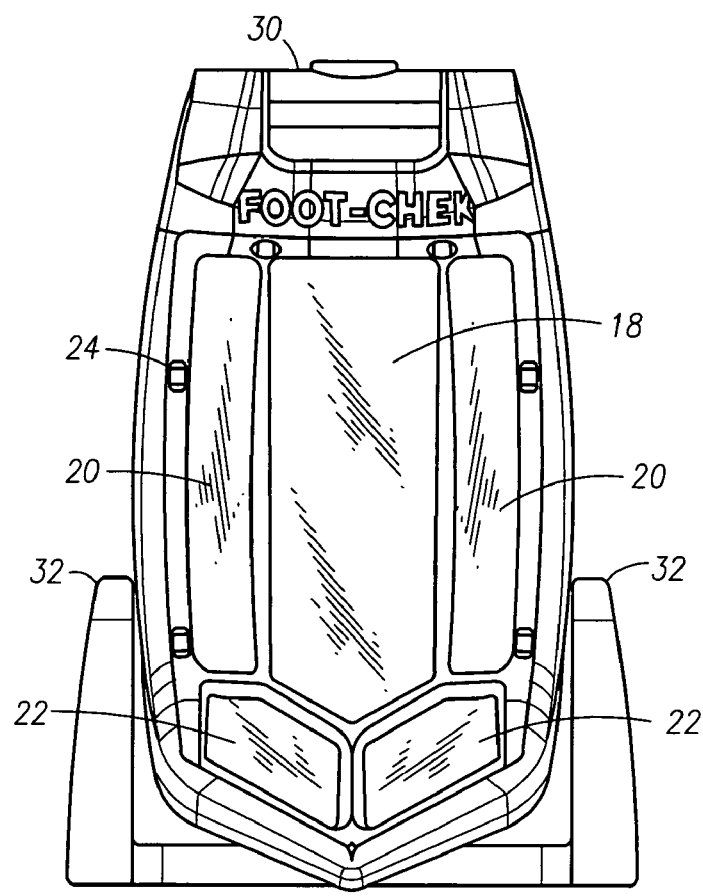
FIG. 2 is a front plan view showing a preferred ornamental design of a foot inspection mirror according to the invention.
Figure 3:
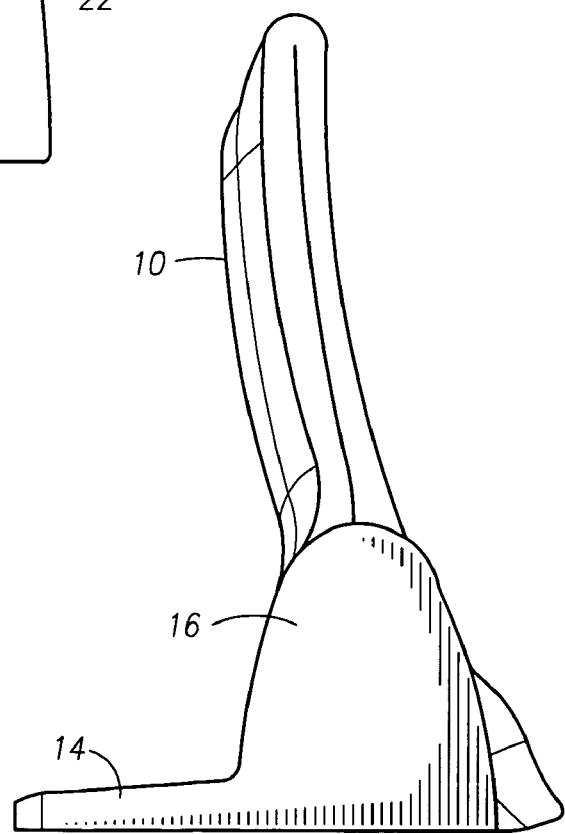
FIG. 3 is a right side plan view of the foot inspection mirror shown in FIG. 2.
Figure 4:
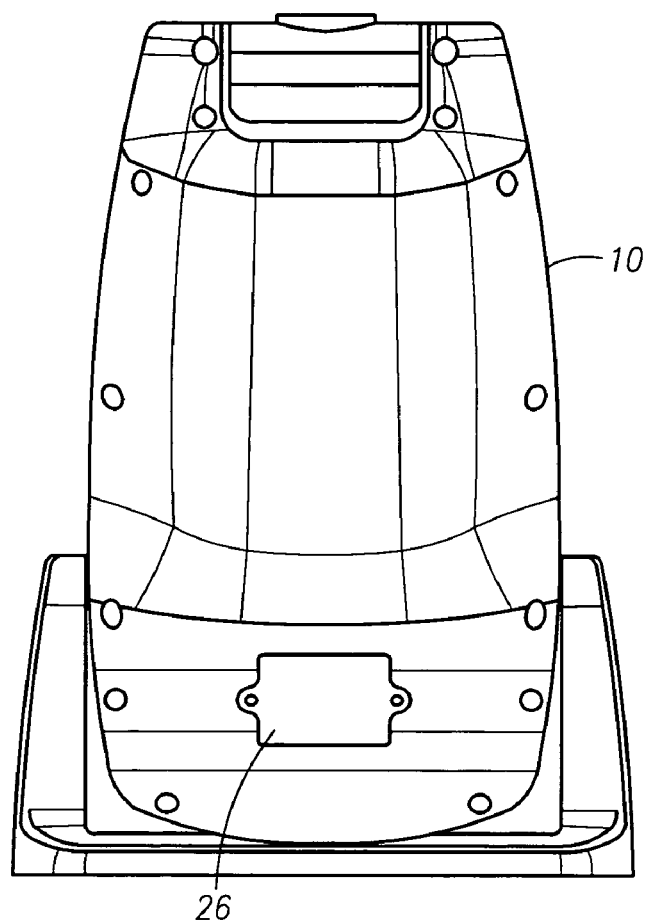
FIG. 4 is a rear plan view of the foot inspection mirror shown in FIG. 2.
Figure 5:
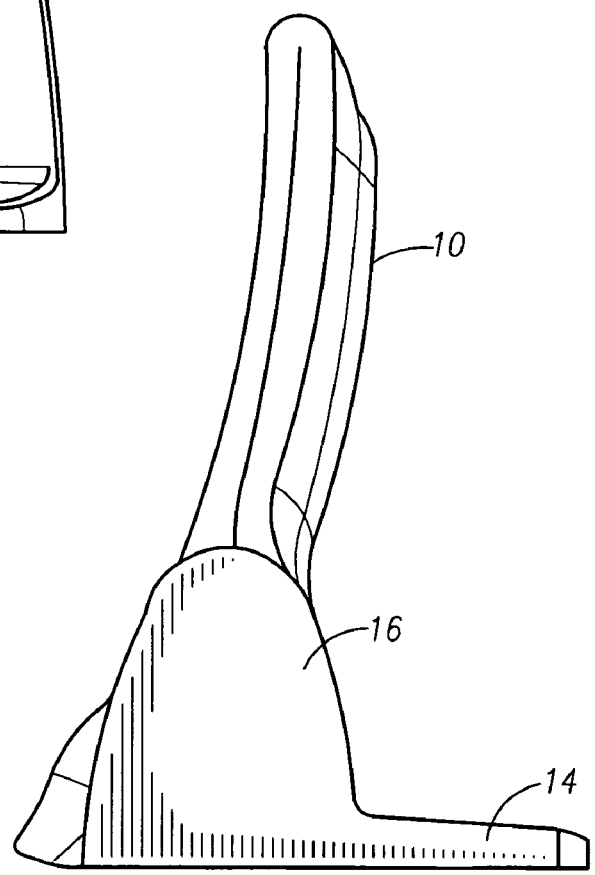
FIG. 5 is a left side plan view of the foot inspection mirror shown in FIG. 2.
Figure 6:
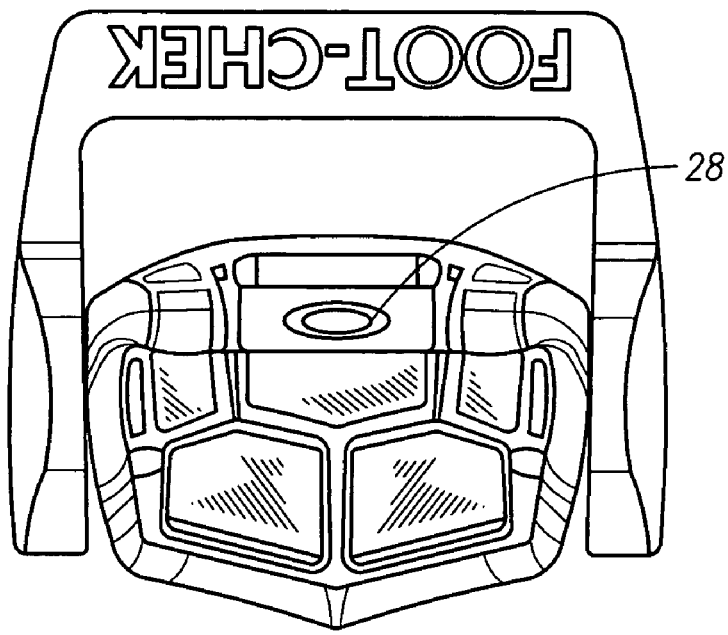
FIG. 6 is a top plan view of the foot inspection mirror shown in FIG. 2.
Figure 7:
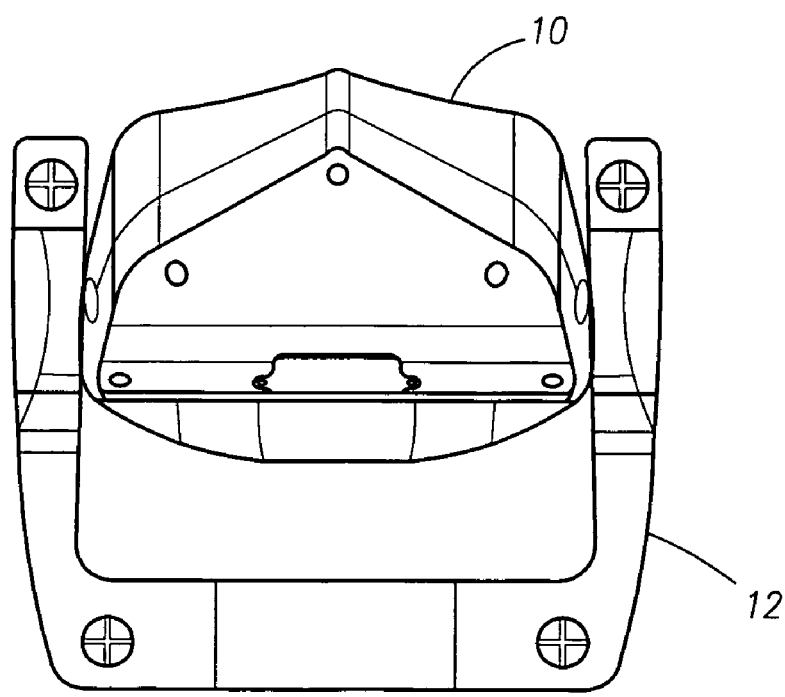
FIG. 7 is a bottom plan view of the foot inspection mirror shown in FIG. 2.

With reference to the accompanying figures, particularly FIG. 1, a foot inspection mirror according to the present invention comprises a mirror assembly portion 10 that is pivotally supported by a stand portion 12. The stand portion 12 comprises a base portion 14 provided to support the foot inspection mirror on floors and flat surfaces. The stand portion further comprises two arm members 16 that are pivotally attached to the lower halves of the vertical sides of the mirror assembly portion 10. The mirror assembly portion 10 is easily tilted to provide the best viewing angle. The stand portion 12 is preferably made of plastic or any other suitable material.

The mirror assembly portion 10 comprises a plurality of mirrors 18, 20, 22 arranged in a fixed array that permits a user to efficiently conduct a visual inspection of the bottom or underside of a foot positioned in front of the mirrors 18, 20, 22. In the preferred embodiment shown in FIG. 1, the array comprises a large mirror 18, which is preferred to be a magnifying mirror having a magnification of about 5X. Two side mirrors 20 are positioned adjacent to the vertical sides of the larger mirror. The side mirrors 20 are angled towards each other. The side mirrors 20 are also magnifying mirrors having preferable 5X magnification to facilitate easy viewing and inspection of the underside and sides of a foot. Two identical smaller mirrors 22 are angled outward and downward with respect to one another and with respect to the larger mirror. The smaller mirrors 22 are also magnifying mirrors that connect at opposing sides. A preferable 5X magnification of the smaller mirrors 22 facilitates easy viewing and inspection of the heel of a foot. The mirrors 18, 20, 22 are preferably coated with a protective polymer coating. The mirror assembly portion 10 is preferably made with plastic or any other suitable material.

The preferred embodiment comprises LED lighting elements 24 arranged around the perimeter of the array of mirrors. The LED lighting elements 24 emit white light at an intensity that is sufficient to illuminate the underside of a user's foot during the inspection process. The LED lighting elements 24 are powered by one or more batteries, which are received in a compartment 26 positioned on the backside of the mirror assembly portion 10. The LEDs 24 can be activated by the user via an easily accessible switch 28 disposed on a handle 30 positioned on the mirror assembly portion 10.

The foot inspection mirror according to the invention is approximately 18 inches tall, when measured from the base 14 of the stand portion 12 to the handle 30 of the mirror assembly portion 10. The foot inspection mirror measures approximately 12 inches wide and 8 inches deep. The mirror assembly portion 10 is connected by pivots 32 to the stand portion 10 such that the large mirror 18 in the array is disposed at an initial angle of about 70° relative to the floor or other flat surface on which the base portion 14 is resting. The mirror assembly portion 10 can pivot over a range of at least 40° (i.e., such that the large mirror 18 in the array is disposed at an angle of about 90° to about 50° relative to the floor or other flat surface on which the base portion 14 is resting). The user can pivot the mirror assembly as needed to fully inspect his or her foot.

2. Operation of the Preferred Embodiment

A foot inspection mirror according to the present invention comprises a mirror assembly portion that is pivotally supported by a stand portion. The stand portion comprises two arm members that are pivotally attached to the lower halves of the vertical sides of the mirror assembly portion. The stand portion further comprises a base portion provided to support the foot inspection mirror on floors and flat surfaces. The stand portion is preferably made of plastic or any other suitable material.

The mirror assembly portion comprises a plurality of mirrors arranged in a fixed array that permits a user to efficiently conduct a visual inspection of the bottom or underside of a foot positioned in front of the mirrors. In the preferred embodiment, the array comprises a large magnifying mirror having a magnification of about 5X. Two magnifying side mirrors are positioned adjacent to the vertical sides of the large mirror. The side mirrors are angled towards each other. The side mirrors are also magnifying mirrors having 5X magnification to facilitate easy viewing and inspection of the underside and sides of a foot. Two identical smaller mirrors are angled outward and downward with respect to one another and with respect to the larger mirror. The smaller mirrors connect at opposing sides. A 5X magnification of the smaller mirrors facilitates easy viewing and inspection of the heel of a foot. The mirrors are coated with a protective polymer coating. The mirror assembly portion preferably made with plastic or any other suitable material.

The preferred embodiment comprises LED lighting elements arranged around the perimeter of the array of mirrors. The LED lighting elements emit white light at an intensity that is sufficient to illuminate the underside of a user's foot. The LED lighting elements are powered by one or more batteries, which are received in a compartment disposed opposite the array of mirrors. The LEDs can be activated by the user via an easily accessible switch disposed on a handle positioned on the top of the mirror assembly portion.

The foot inspection mirror according to the invention is approximately 18 inches tall, when measured from the base of the stand portion to the handle of the mirror assembly portion. The foot inspection mirror measures approximately 12 inches wide and 8 inches deep. The mirror assembly portion is pivotally connected to the stand portion such that the large mirror in the array is disposed at an initial angle of about 70° relative to the floor or other flat surface on which the base portion is resting. The mirror assembly portion can pivot over 40° to a comfortable angle between 50° and 90° relative to the floor. The user can pivot the mirror assembly as needed to fully inspect his or her foot.

To use the present invention, a person preferably places the foot inspection mirror on a floor or other flat surface. The user chooses to either comfortably sit or stand at a position approximate to the device. The user turns on the LED lights by means of the switch positioned on a handle. The user adjusts the mirror assembly portion at its pivot to provide for the best viewing angle. The user places one foot in front of the mirrors to obtain an illuminated and magnified view of the heel, sides and underside of the foot. The entire foot can be viewed at one time without any unnecessary bending, maneuvering or strain on the user. The visual inspection only takes seconds. The user repeats the inspection process for the other foot. If the user detects any abnormalities, s.a. sores, calluses, infections, etc., he or she can immediately contact a physician for treatment, the detection and treatment of which will prevent any severe health problems from arising. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

Having thus described the invention what is claimed as new and desired to be secured by Letters Patent is as follows:

1. A foot inspection mirror comprising a mirror assembly portion pivotally supported to a base portion, said mirror assembly portion consists of a large mirror, two identical side mirrors and two identical small mirrors, wherein the tops of said two small mirrors are positioned adjacent to the bottoms of said large mirror and said side mirrors and said two side mirrors are positioned adjacent to the vertical sides of said large mirror at an angle towards one another.

2. The foot inspection mirror of claim 1, wherein said two small mirrors are angled outward and downward with respect to each other and with respect to said large mirror.

3. The foot inspection mirror of claim 1, further comprising LED lighting elements arranged around the perimeter of said mirrors on said mirror assembly portion.

4. The foot inspection mirror of claim 3 wherein said LED lighting elements emit white light at an intensity sufficient to illuminate the underside of a foot during a visual inspection of said foot.

5. The foot inspection mirror of claim 3, wherein said LED lighting elements are powered by one or more batteries received in a compartment disposed opposite an array of said mirrors.

6. The foot inspection mirror of claim 3, wherein said LED lighting elements can be activated by an easily accessible switch disposed on a handle positioned at the top of said mirror assembly portion.

7. The foot inspection mirror of claim 1, wherein said mirror assembly portion is pivotally connected to a stand portion such that said large mirror in an array of mirrors is disposed at an initial angle of about 70° relative to a floor or another flat surface on which said base portion is resting.

8. The foot inspection mirror of claim 1, wherein said mirror assembly portion can pivot over a range of at least 40°.

9. The foot inspection mirror of claim 8, wherein said large mirror in an array of mirrors can pivot at an angle from about 50° to about 90° relative to a floor or another surface on which said base portion is resting.

10. The foot inspection mirror of claim 1, wherein a measure of the height of said foot inspection mirror is approximately 18 inches from a base of a stand portion to a handle on said mirror assembly portion.

11. The foot inspection mirror of claim 1, wherein a measure of the width of said foot inspection mirror is approximately 12 inches.

12. The foot inspection mirror of claim 1, wherein a measure of the depth of said foot inspection mirror is approximately 8 inches.

13. The foot inspection mirror of claim 1, wherein said mirror assembly portion is pivotally attached at the lowers halves of its vertical sides to two arms on said base portion.

14. The foot inspection mirror of claim 1, wherein said base portion is made of a plastic material.

15. The foot inspection mirror of claim 1, wherein said mirror assembly portion is made of a plastic material.

16. The foot inspection mirror of claim claim 1, wherein said mirrors are coated with a protective polymer coating.

17. The foot inspection mirror of claim 1, wherein said mirrors are magnifying mirrors having a 5X magnification.

* * * * *